United States Patent
Schlienger et al.

(10) Patent No.: US 8,568,350 B2
(45) Date of Patent: Oct. 29, 2013

(54) BREAST SHIELD FOR EXPRESSING HUMAN BREAST MILK

(75) Inventors: André Schlienger, Maschwanden (CH); Etienne Furrer, Zug (CH); Beda Weber, Sins (CH); Brian H. Silver, Cary, IL (US); Daniela Wäckerlin, Baar (CH); Gamal Khalil, Baar (CH)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 13/497,351

(22) PCT Filed: Sep. 17, 2010

(86) PCT No.: PCT/CH2010/000226
§ 371 (c)(1),
(2), (4) Date: Mar. 21, 2012

(87) PCT Pub. No.: WO2011/035448
PCT Pub. Date: Mar. 31, 2011

(65) Prior Publication Data
US 2012/0316493 A1    Dec. 13, 2012

Related U.S. Application Data

(60) Provisional application No. 61/244,636, filed on Sep. 22, 2009.

(51) Int. Cl.
*A61M 1/06* (2006.01)
(52) U.S. Cl.
USPC .......................................................... 604/74
(58) Field of Classification Search
USPC .......................................................... 604/74
See application file for complete search history.

(56) References Cited

U.S. PATENT DOCUMENTS

| 949,414 A | 2/1910 | Cunningham |
| 4,799,922 A | 1/1989 | Beer et al. |

(Continued)

FOREIGN PATENT DOCUMENTS

| WO | 96/22116 | 7/1996 |
| WO | 99/44650 | 9/1999 |

(Continued)

OTHER PUBLICATIONS

English Translation of the Int. Preliminary Report on Patetablity for Int. App. No. PCT/CH2010/000225, mailed Apr. 12, 2012.

(Continued)

*Primary Examiner* — Aarti B Berdichevsky
(74) *Attorney, Agent, or Firm* — McDonnell Boehnen Hulbert & Berghoff LLP (57) ABSTRACT

A breast shield has a tubular connector and a funnel that is integrally formed thereon, and is intended for resting on a mother's breast. The funnel widens toward the free side thereof which faces away from the connector. A passage, which extends continuously from a breast-side end of the funnel as far as a pump-side end, being opposite the breast-side end, of the connector, and serves to apply a vacuum to the mother's breast and for the flowing away of the expressed breast milk. The funnel is of more flexible design than the connector, and the funnel has a main region extending over a substantial part of the length thereof with a first opening angle of the passage, and a breast-side end region with a second opening angle of the passage. When not in use, the first opening angle is smaller than the second opening angle. In use, at least the first opening angle can be enlarged by axial pressure on the breast shield. The breast shield is pleasant to wear and minimizes the dead volume.

15 Claims, 4 Drawing Sheets

(56) References Cited

U.S. PATENT DOCUMENTS

| | | |
|---|---|---|
| 4,857,051 A | 8/1989 | Larsson |
| 4,929,229 A | 5/1990 | Larsson |
| 5,601,531 A | 2/1997 | Silver |
| 6,161,710 A | 12/2000 | Dieringer et al. |
| 6,379,327 B2 | 4/2002 | Lundy |
| 6,440,100 B1 | 8/2002 | Prentiss |
| 6,461,324 B1 | 10/2002 | Schlensog |
| 6,663,587 B2 | 12/2003 | Silver et al. |
| 6,669,064 B2 | 12/2003 | Perricone |
| 7,094,217 B2 | 8/2006 | Fialkoff |
| 7,223,255 B2 | 5/2007 | Myers et al. |
| 7,559,915 B2 | 7/2009 | Dao et al. |
| 7,662,127 B2 | 2/2010 | Silver et al. |
| 2004/0087898 A1 | 5/2004 | Weniger |
| 2005/0154349 A1 | 7/2005 | Renz et al. |
| 2005/0222536 A1 | 10/2005 | Silver |
| 2006/0106334 A1 | 5/2006 | Jordan et al. |
| 2007/0078383 A1 | 4/2007 | Tashiro et al. |
| 2008/0039781 A1 | 2/2008 | Bjorge |
| 2008/0146118 A1 | 6/2008 | Solberg et al. |
| 2008/0171970 A1 | 7/2008 | Luzbetak et al. |
| 2008/0243059 A1 | 10/2008 | Yamashita et al. |
| 2008/0255503 A1 | 10/2008 | Quackenbush et al. |
| 2008/0287037 A1 | 11/2008 | Solberg |
| 2009/0062731 A1 | 3/2009 | Keyong et al. |
| 2009/0099511 A1 | 4/2009 | Sutrina et al. |

FOREIGN PATENT DOCUMENTS

| | | |
|---|---|---|
| WO | 02/102437 | 12/2002 |
| WO | 2005/067997 | 7/2005 |
| WO | 2008/008781 | 1/2008 |
| WO | 2008/057218 | 5/2008 |
| WO | 2008/090386 | 7/2008 |
| WO | 2008/137678 | 11/2008 |

OTHER PUBLICATIONS

English Translation of the Int. Preliminary Report on Patetablity for Int. App. No. PCT/CH2010/000226, mailed Apr. 12, 2012.
International Search Report for Int. App. No. PCT/US2010/049355 mailed May 16, 2011.
International Search Report for International Patent App. No. PCTICH2010/000226, dated Jan. 4, 2011.
International Search Report for International Patent App. No. PCTICH2010/000225, dated Jan. 12, 2011.

BREAST SHIELD FOR EXPRESSING HUMAN BREAST MILK

CROSS REFERENCE TO RELATED APPLICATIONS

The present application is a U.S. National Phase Application pursuant to 35 U.S.C. §371 of International Application No. PCT/CH2010/000226 filed Sep. 17, 2010, which claims priority to U.S. Provisional Patent Application No. 61/244,636 filed on Sep. 22, 2009. The entire disclosure contents of these applications are herewith incorporated by reference into the present application.

TECHNICAL FIELD

The present invention relates to a breast shield for expressing human breast.

BACKGROUND

Devices for expressing human breast milk are well known. In principle, there are two different types: the first device type is operated manually, i.e. the negative pressure required for the expressing operation is generated by manual actuation of the vacuum pump. In the devices of the second type, the vacuum pump is operated electrically, it being possible for the vacuum pump to be connected to the power supply network and/or to be operated via a battery or another energy accumulator. Examples for this include WO 96/22116, US 2009/0099511, US 2008/0287037, U.S. Pat. No. 7,094,217 and US 2008/0039781.

The vacuum pumps are connected to a breast shield either directly or via vacuum lines. The breast shield usually has a funnel-shaped part for receiving part of the mother's breast including the nipple. As a rule, the funnel-shaped part merges into a part, which is in the shape of a hollow cylinder and to which, firstly, either the vacuum pump is connected directly or via a suction line and which, secondly, is likewise connected directly or via a milk line to a milk collecting container. It is known to select breast shields in accordance with the size of the breast. In particular breast shield sets are known, in which the size of the funnel-shaped part can be selected according to the mother.

Relatively small breast shields are also known in the prior art. U.S. Pat. No. 6,379,327 discloses a portable, "hands-free" expressing device. In this context, "hands-free" means that, once switched on, the entire device functions without hands, i.e. that neither the pump nor the breast shield have to be held by hand. In US '327, a small funnel-shaped breast shield is fastened for this purpose to the breast using straps. A first tube leads from the breast shield to a vacuum pump, which is held in a belt. A second tube leads from the breast shield into a milk collecting container, which can be carried in the same belt.

WO 02/102437 and WO 2008/137678 show "hands-free" expressing devices. The breast shield here is in each case integrated in a pump housing and serves at the same time as a diaphragm for generating a negative pressure.

U.S. Pat. No. 949,414 describes a funnel-shaped breast shield, which can be arranged under a bra. Rather than a vacuum being applied, a tube leads from the breast shield to a baby who is intended to obtain the milk desired by sucking on the tube.

U.S. Pat. No. 6,440,100 shows a device for expressing breast milk with a small breast shield that can be worn under the bra. A milk tube leads from the breast shield to a milk collecting container. The container is connected via a vacuum tube to a vacuum source. The milk collecting container is evacuated by means of the vacuum source, with the negative pressure being applied to the breast shield via the milk tube. Because of the negative pressure prevailing in the milk collecting container, expressed milk is now intended to pass into the milk collecting container via the milk tube. As an alternative, the milk collecting container itself can serve as a vacuum pump. The device has the disadvantage that the relatively large volume of the milk collecting container likewise has to be evacuated. The "dead volume" considerably restricts the productivity of the device.

SUMMARY

It is an object of the invention to provide an improved breast shield, which is pleasant for the mother to wear and which minimizes the air-filled dead volume.

The breast shield according to the invention has a tubular connector and a funnel that is integrally formed thereon and is intended for resting on a mother's breast. The funnel widens toward the free side thereof that faces away from the connector, and a passage extends continuously from a breast-side end of the funnel as far as a pump-side end, being opposite the breast-side end, of the connector, which serves to apply a vacuum to the mother's breast and for the flowing away of the expressed breast milk. According to the invention, the funnel is more flexible than the connector. The funnel has a main region extending over a substantial part of the length thereof with a first opening angle of the passage, and a breast-side end region with a second opening angle of the passage. When not in use, the first opening angle is smaller than the second opening angle. In use at least the first opening angle can be enlarged by axial pressure on the breast shield.

The breast shield adapts itself optimally to the shape of the human mother's breast and creates a tight or less tight connection to the breast, depending on requirements and contact pressure, respectively.

It is pleasant to wear and reduces the air-filled or milk-filled dead volume due to its adaptability.

The breast shield is preferably designed to be small so that it merely surrounds the nipple and at maximum the aerola. Not only can the breast shield be used in a simple manner in a "hands-free" system, for example it can be kept in a bra, the breast shield also has scarcely any air-filled regions because of its small size. This has a positive effect on the vacuum pump since the pump requires less power and can therefore operate more quietly. Furthermore, for this reason, the vacuum pump can also be made smaller.

In addition, these small breast shields have the advantage that there can be less movement of the tissue of the breast within the shield. As a result, the breast shields can bear more tightly against the tissue. A lower pumping power is required in turn as a result. The pump likewise can be designed to be smaller and operate more quietly.

In contrast to the known breast shields and to the natural sucking of a baby, the nipple in the breast shield according to the invention is customarily not expanded to 2.5 times the length thereof. This is pleasant for the mother, in particular if she has painful nipples.

When not in use, typical values of the first opening angle of the breast shield are <5° (smaller or equal 5°) and of the second opening angle are 90° to 160°. During use and depending on the axial pressure applied, at least the second opening angle can be enlarged up to 120° or preferably up to 160°.

The funnel preferably has a breast-side diameter of 5 mm to 40 mm and a length of 10 mm to 40 mm, such that, in use, the nipple, and at maximum the areola, is surrounded by the breast shield. Milk ducts in the breast tissue are preferably not surrounded by the breast shield.

Between the connector and funnel, there is preferably a transition region with a third opening angle of the passage, wherein the third opening angle is larger than the first opening angle when the device is not in use.

Typical values of the third opening angle are 60° to 150°.

The main region preferably directly adjoins the transition region. The end region preferably also directly adjoins the main region.

In a preferred embodiment, the connector has a wall thickness which is much greater than the wall thickness of the funnel. As an addition or alternatively, the connector may also be formed from a material having greater shore hardness.

In the transition region between the connector and funnel there is preferably an outer stop, which protrudes over the outer circumference of the connector.

The connector can be readily inserted into a recess if the outer circumference of the connector is designed such that it widens conically toward the funnel.

The breast shield according to the invention is preferably manufactured from silicone and preferably has a Shore A hardness of 30 to 70. The funnel preferably has a Shore A hardness of about 50 and the connector has a shore A hardness of about 70.

So that the relatively small and compact breast shield can be readily held in the hand, the breast shield is preferably provided in a breast shield set with a coupling part. The coupling part serves to receive the breast shield connector in a sealing manner, wherein the coupling part is of cylindrical design and is closed on one side by a base such that a blind hole for receiving the connector is formed. There is at least one, and in one embodiment exactly one, port opening, which is connected to the passage of the breast shield in terms of fluid communication.

In the assembled state, an end side of the connector remote from the breast shield preferably ends at a distance from the base of the coupling part. The at least one port opening is preferably arranged eccentrically in the coupling part.

If the at least one port opening is arranged in an upper region of the coupling part and the coupling part has a marking which defines "this side up" in the space, then, during the expressing operation, stationary air bubbles are avoided in the coupling parts and air-filled dead spaces are eliminated.

In order to be able to insert the conical connector more simply, the blind hole of the coupling part also tapers in diameter toward the base.

The coupling part is preferably of stiff design, which facilitates the insertion of the connector and increases the stability. The part can therefore be more easily held or fastened.

The breast shield in one embodiment does not have any inserts and consists merely of the abovementioned elements.

The breast shield according to the invention can be combined with all types of breast pumps. However, the use thereof with a breast pump, which changes from a pneumatic system into a hydraulic system during the expressing operation, is advantageous. Thus, the same line, which has initially applied the vacuum to the breast shield, also serves to transport the expressed milk and therefore the milk becomes the medium, which generates the further flow of milk out of the mother's breast.

Such a device for expressing human breast milk has the breast shield according to the invention for bearing against a mother's breast, a vacuum pump for generating a vacuum, a line which connects the breast shield to the pump chamber and is intended for transmitting the vacuum generated to the breast shield, and a chamber. The line ends on the pump side in a first port of the chamber. According to the invention, the chamber has a second port for connection to a milk collecting container. The two ports in the chamber are connected to each other in terms of fluid communication. During the expressing operation, the line forms a milk line for transporting breast milk expressed in the breast shield to the chamber. The milk is subsequently conducted from the chamber to the milk collecting container.

An advantage of the system is that the already expressed milk warms the breast shield, which is pleasant for the mother. Furthermore, only a single line is required, which in "hands-free" designs in particular can be discreetly hidden in the clothing.

Since the entire system is flooded by milk and there is therefore no longer a vacuum line in the classic sense, a lower pumping power is required in order to express breast milk. Typical values for the air output are at maximum 50 ml/min and for the milk output at maximum 100 ml/min. The vacuum pump can therefore be configured to be smaller and lighter, so as to be less conspicuous to onlookers. The mother can therefore use said vacuum pump more discreetly. In addition, because of to the lower pumping power requirement, the vacuum pump is quieter during use, which increases the comfort and discretion.

Since the entire system, i.e. the entire system apart from the pumping-unit-side or drive-side region of the vacuum pump, is flooded with milk and there are only very small air-filled dead spaces, if any at all, the applied vacuum can more easily be controlled. The negative pressure present at the breast shield also corresponds more to the vacuum generated in the vacuum pump.

The milk line can be realized in various ways. In a preferred embodiment, there is a partition wall which separates a vacuum pump drive and the line from each other. As a result, the chamber is divided by the partition wall into a breast-shield-side region and a drive-side region. The two regions are completely separated from each other and are connected to each other only via the diaphragm. Therefore, milk does not pass into the drive-side region of the vacuum pump, nor does dirt or air from the drive-side region pass into the milk-conducting line and therefore into the breast shield and the milk collecting container. The partition wall is preferably a diaphragm.

In a preferred embodiment, the diaphragm is driven and serves to convey the expressed milk. As a result, the milk can be expressed independently of the relative position of the breast shield, the milk collecting container and the vacuum pump with respect to one another. The mother may, for example, even express milk while lying down. This is optimum in particular in a "hands-free" embodiment since the mother may bend down and in general move very freely.

A very wide variety of vacuum pumps can be used with the vacuum-transmitting and milk-conducting line according to the invention. Preferably, but not necessarily, a single diaphragm is used in each case both for transporting the milk and for separation of the media.

The vacuum pump is preferably a diaphragm pump, wherein the chamber is the vacuum-generating pump chamber of the vacuum pump, and the diaphragm is the diaphragm of the pump chamber used for generating the vacuum.

The breast shield can also be connected directly and without the above-described line to a housing of a vacuum pump. Nevertheless, the change can be made to a hydraulic pump system. A preferred vacuum pump for expressing human breast milk by means of this breast shield has a drive and a diaphragm that can be driven cyclically by the drive, the diaphragm being arranged in a chamber, the diaphragm separating the chamber into a drive-side part and a breast-shield-side part, and the breast-shield-side part having a vacuum port for producing a connection to the breast shield. According to the invention, the breast-shield-side part of the chamber furthermore has a milk port for producing a connection to a milk collecting container, and the vacuum port and the milk port are connected to each other in terms of fluid communication via the breast-shield-side part of the chamber. Preferably, the vacuum pump is a diaphragm pump and the chamber is the vacuum-generating pump chamber.

In a preferred embodiment, the vacuum pump is an electric diaphragm pump. In this case, the diaphragm of the diaphragm pump preferably forms the above-mentioned diaphragm serving as a drive for the milk and as a partition wall. The drive of the diaphragm preferably serves simultaneously to generate the vacuum in the pump chamber and to convey the flow of milk. Owing to the triple function of the diaphragm, the vacuum can be better controlled.

The diaphragm preferably has a substantially circular outline. The diaphragm is preferably driven in the central region thereof, preferably in the center thereof.

Other types of diaphragm pumps and alternative pumps without a diaphragm may also be used. Furthermore, manually driven pumps may be used.

The combination of the three elements a vacuum-transmitting and milk-conducting line, a pump chamber diaphragm with its triple function, and the breast shield that is of small design and avoids dead volumes results in a device that can be designed to be small and quiet, and furthermore is optimally suitable for any type of use, in particular "hands-free" use.

Further advantageous embodiments and variants of the method are indicated in the dependent claims.

BRIEF DESCRIPTION OF THE DRAWINGS

Preferred embodiments of the invention are described below with reference to the drawings that serve merely for explanation and should not be interpreted as being limiting. In the drawings.

The same parts are provided with the same designations in the Figures.

DETAILED DESCRIPTION

Figure 1:
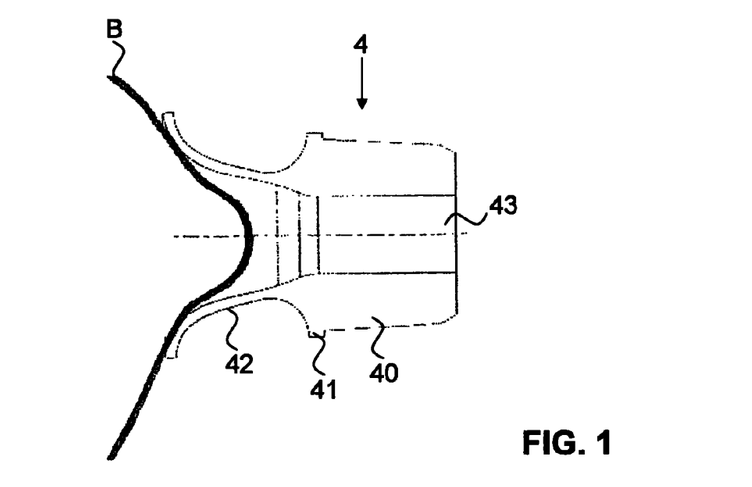
FIG. 1 shows a longitudinal section through a breast shield according to the invention, applied to a human breast with a relatively large contact pressure.
Figure 2:
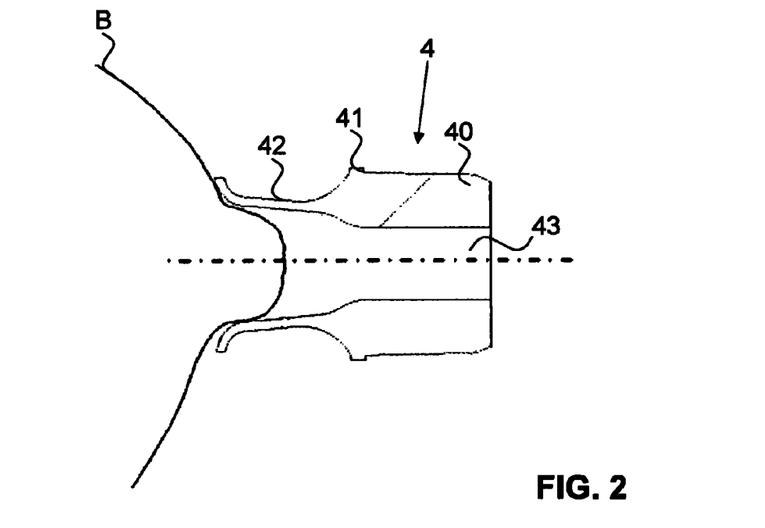
FIG. 2 shows a longitudinal section through the breast shield according to the invention according to FIG. 1, applied to a human breast with a smaller contact pressure.
Figure 3:
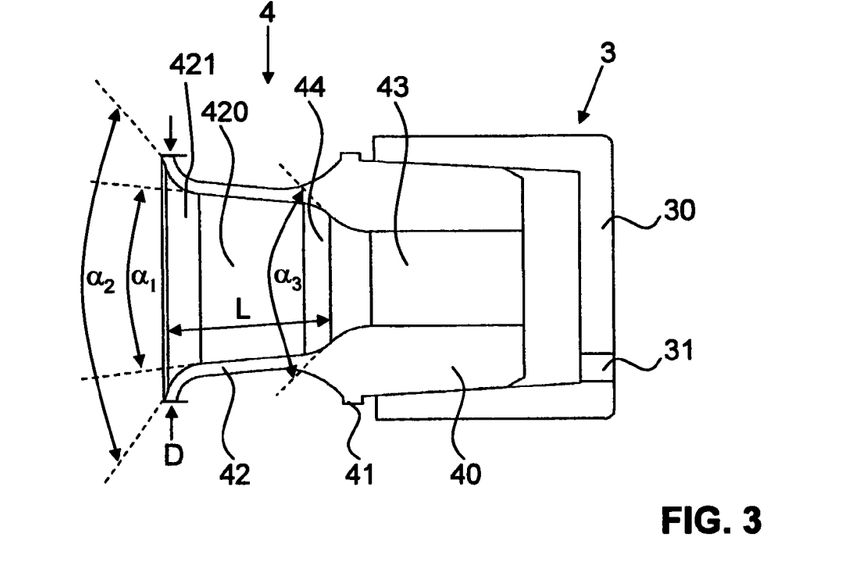
FIG. 3 shows a longitudinal section through the breast shield according to FIG. 1 with a coupling part in a first embodiment.

FIGS. 1 to 3 illustrate a preferred example of a breast shield 4 according to the invention. FIG. 3 shows a breast shield set with the coupling part 3.

FIG. 1 shows the breast shield 4 according to the invention applied to a female breast B. The breast shield 4 has a connector 40, a funnel 42 and a transition region 44 connecting the connector 40 and the funnel 42. There is preferably a radially outwardly protruding flange 41 between the connector 40 and funnel 42. A continuous passage 43 extends through the entire breast shield 4 such that the breast shield is designed to be open at two opposite ends. The breast shield 4 is preferably of rotationally symmetrical design. In one embodiment, the breast shield 4 does not have any further elements, such as inserts, for example.

The breast shield 4 is preferably designed as a single piece, and is composed of plastic, preferably of silicone, for example.

The connector 40 is of solid design, i.e. relatively stiff design, and serves for the coupling to the coupling part 3. The connector 40 has a wall thickness which is much greater than the wall thickness of the funnel 42. In this example, the connector 40 is of conical design at the outer circumference thereof while the connector is preferably of rotationally symmetrical design. The conicity facilitates the insertion into the coupling part 3 and also increases the tightness of the connection to the coupling part 3. The tightness is furthermore obtained by the connector 40, due to the material, being slightly compressed in the coupling part. For this purpose, the outside diameter of the connector 40 is slightly larger than the inside diameter of the coupling part 3. Example external diameters of the connector 40 are 8 mm to 40 mm. Example lengths are 5 mm to 40 mm.

The funnel 42 serves to receive the mother's breast. The funnel is preferably configured to be highly flexible. The funnel is of substantially more flexible and soft design than the connector 40. Because of the flexibility, the funnel adapts its shape to the shape of the breast. The funnel has a wall thickness which is many times smaller than the wall thickness of the connector 40. Alternatively, the connector 40 and funnel 42 may also have the same wall thickness, wherein, in this case, the connector 40 is preferably manufactured from a material having a greater Shore hardness or has reinforcement. The funnel 42 preferably has a Shore A hardness of about 50 and the connector 40 has a Shore A hardness of about 70.

FIG. 3 illustrates the breast shield 4 when not in use. The funnel 42 has at least two regions: a main region 420 and a front, breast-shield-side end region 421. The end region 421 forms the breast-shield-side end of the breast shield and therefore ends freely.

When not in use, the main region 420 has a first opening angle $\alpha_1$ and the end region has a second opening angle $\alpha_2$. The first opening angle $\alpha_1$ is smaller than the second opening angle $\alpha_2$. In addition, the wall is preferably bent over outward in the end region 421. As can be seen in FIGS. 1 and 2, the first opening angle $\alpha_1$ can be enlarged upon axial contact pressure on the breast such that the end region 421 adapts itself optimally to the shape of the breast.

As can be seen in the figures, the main region 420 directly adjoins the end region 421. At the other end, the main region 420 directly adjoins the transition region 44.

In the transition region 44 there is a further, third opening angle $\alpha_3$, which is likewise larger than the first opening angle of the main region 420. The third opening angle serves as a predetermined value for the main region for enlarging the angle.

The angles when not in use are preferably, for the first opening angle $\alpha_1$ <5°, for the second opening angle $\alpha_2$, 90° to 160° and for the third opening angle $\alpha_3$, 60° to 150°. When in use, at least the first opening angle $\alpha_1$ can be enlarged preferably to an angle of up to 10°.

The funnel 42 has a length L of 10 mm to 40 mm. The diameter D in the front end region is preferably 5 mm to 40 mm, in particular 20 mm to 40 mm. As a result, the funnel 42 is so small, that the funnel surrounds only the nipple or in addition, at the most a portion or all of the areola of the breast. This corresponds approximately to the portion of the breast that is taken into the mouth by a baby. The funnel 42 is of frustoconical design in the region of the connector 40, said funnel opening toward the breast. The front, breast-side border thereof is inclined outward to a greater degree than the connector-side part.

Since the breast shield 4 or at least the funnel 42 is configured to be flexible, the mother, by choosing the contact pressure, can select how much of the breast is actually surrounded by the breast shield 4. The contact pressure is produced from the axial pressure on the funnel 42 and the counterpressure from the mother's breast. In FIG. 1, the contact pressure is relatively large and the funnel is expanded, and, in FIG. 2, the pressure is smaller and the funnel 42 merely encloses the nipple. By choosing the contact pressure, the tightness of bearing against the breast can also be adjusted and therefore the expressing operation can be adjusted to be as comfortable as possible for the mother.

As can be seen in FIG. 3, the breast shield 4 is plugged into the coupling part 3. The coupling part 3 is preferably likewise configured to be small, but to be as stiff as possible. In the outer circumference thereof, the coupling part is preferably of cylindrical design and, in the inner circumference thereof, is frustoconical or conical, respectively. The coupling part 3 has a U-shaped cross section, i.e. is designed to be open at one end and closed at the opposite end. There is therefore a blind hole into which the connector 40 of the breast shield 4 can be pushed as far as the stop 41. In FIG. 3, the breast shield 4 is not yet fully pushed in. As can be seen, however, in the fully-pushed in state, there is a gap between the end side of the connector 40 and the rear wall of the coupling part 3, the gap forming a fluid passageway from the passage 43 to a port opening 31 in the coupling part 3.

The port opening 31 serves for the connection of a vacuum line and/or milk line. If the vacuum line and milk line run separately from each other, there are therefore two port openings in the coupling part 3. The port openings may be provided with nonreturn valves. The vacuum line leads to the vacuum pump and the milk line to the milk collecting container.

The lines can simply be plugged into the openings. However, they may also be connected fixedly to the coupling part 3, or there may be plug-in or plug-on means, for example connectors, for connection to the lines.

Figure 4:
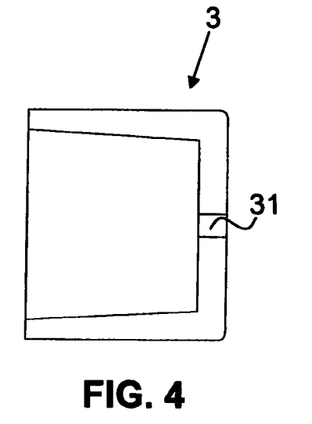
FIG. 4 shows a longitudinal section through a coupling part in a second embodiment.
Figure 5:
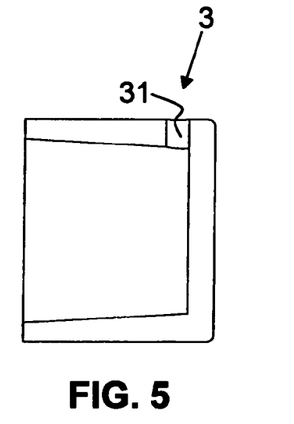
FIG. 5 shows a longitudinal section through a coupling part in a third embodiment.
Figure 6:
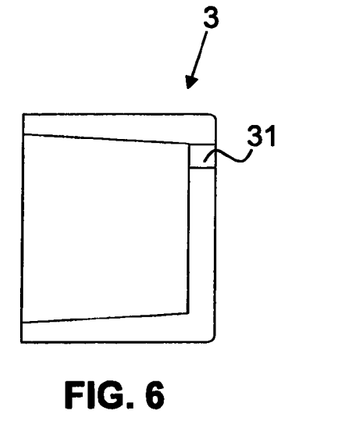
FIG. 6 shows a longitudinal section through the coupling part according to FIG. 3.

The at least one port opening 31 may be provided at different locations. In FIG. 3, the port opening 31 is arranged in the upper region in the rear wall of the coupling part 3. In FIG. 4, the port opening 31 is arranged centrally in the rear wall. In FIG. 5, the port opening 31 is arranged in the casing, but in the rear region close to the rear wall, and is preferably arranged in the upper region. FIG. 6 once again shows the situation according to FIG. 3, but without the breast shield 4 plugged in.

If the port opening 31 in particular for the milk line is arranged at the top, the residual air in the coupling part 3 is sucked off together with the milk and the dead volume is reduced once again. In use, the breast shield 4 and coupling part 3 no longer have any air chambers. The clearances thereof, if still present, are filled with milk. So that the port opening 31 is actually directed upward during use, a corresponding marking, for example, can be indicated on the coupling part 3.

The breast shield can be used with all types of breast pumps. However, it is advantageous when used with the devices illustrated in FIGS. 7 to 9 for expressing human breast milk.

Figure 7:
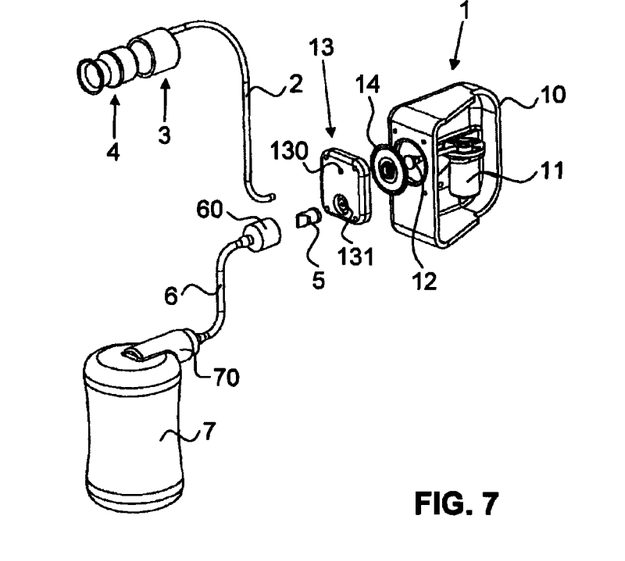
FIG. 7 shows an exploded view of a device according to the invention for expressing human breast milk in a first embodiment, in which a side wall of the vacuum pump is not illustrated.
Figure 8:
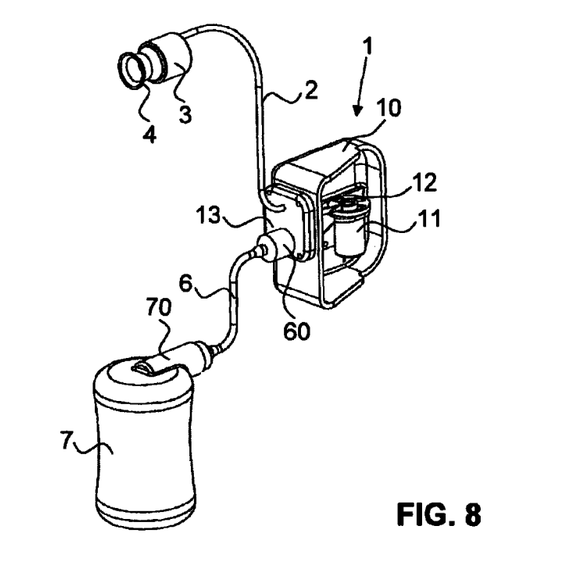
FIG. 8 shows the device according to FIG. 7 assembled for use, in which a side wall of the vacuum pump is not illustrated.

FIGS. 7 and 8 illustrate a first embodiment of a device of this type. The device has a vacuum pump 1, a first line 2, the coupling part 3, the breast shield 4, a nonreturn valve 5, a second line 6 and a milk collecting container 7.

The breast shield 4 is connected to the vacuum pump 1 via the coupling part 3 and the first flexible line 2. The second flexible line 6 leads from the vacuum pump 1 to the milk collecting container 7, the connection being provided with the nonreturn valve 5. The two flexible lines 2, 6 are preferably tubes, in particular made of silicone.

Figure 9:
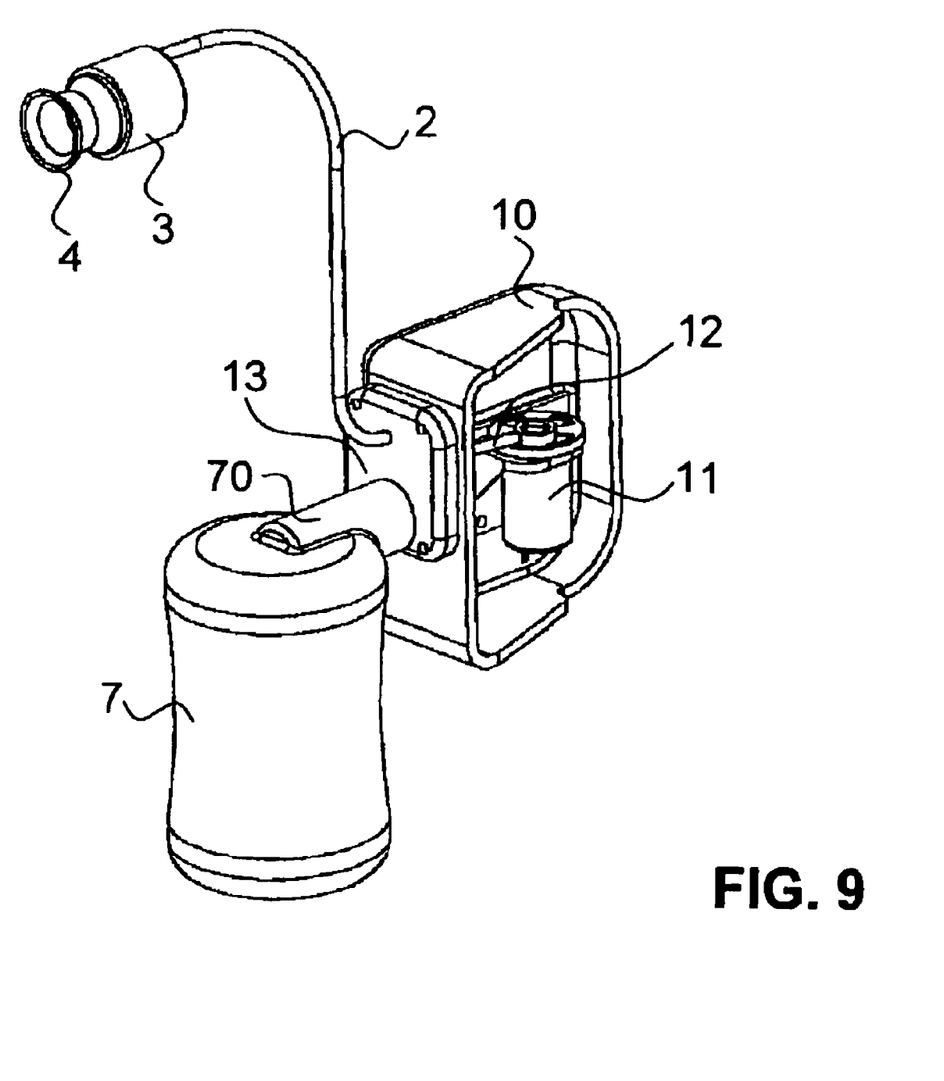
FIG. 9 shows a device according to the invention in a second embodiment, in which a side wall of the vacuum pump is not illustrated.

As illustrated in FIG. 9, the milk collecting container 7 may alternatively also be fastened directly to the vacuum pump 1. For this purpose, there is preferably a suitably shaped adapter 70 on the milk collecting container 7, its adapter being detachably connectable to a housing 10 of the vacuum pump.

The vacuum pump 1 has the abovementioned housing 10, a side wall of the housing 10 not being illustrated in the drawings. As a result, the interior of the housing 10 can be revealed.

There is an electric motor 11 in the housing 10. The electric motor can be operated from the electric supply network and/or the motor can be battery operated. A force transfer unit 12, here a connecting rod connected to the motor, transfers the rotational movement of the motor into a linear movement. The connecting rod 12 is connected at the second end thereof to a diaphragm 14. The diaphragm 14 is arranged in a recess of the housing 10, which forms part of a pump chamber. A cover 13 which is detachably connectable to the housing 10 secures the diaphragm 14 in its position.

Instead of the drive, other types of drives, in particular manual drives, can also be used.

The cover 13 is preferably screwed to the housing 10. Other types of connection are likewise possible. The cover 13 likewise has a recess such that the cover forms a second part of the pump chamber. The two parts of the pump chamber are separated from each other by the diaphragm 14. The cover can be formed as a single piece or as a number of pieces.

The cover 13 can be formed as a single piece or as a number of pieces. The cover forms not only a tight closure but also serves as a valve plate for the diaphragm vacuum pump. Passages and valves (not illustrated in detail here) which enable the vacuum to be built up in the cover- or breast-side part of the pump chamber are therefore arranged in the cover 13.

The operation of the diaphragm pump is not described in detail here since it is well known. By means of a drive, here by means of a motor 11 and connecting rod 12, the diaphragm is moved cyclically to and fro such that a negative pressure is generated in the breast-shield-side or cover-side part of the pump chamber. Instead of the drive illustrated here, other types of drive suitable for moving the diaphragm 14 cyclically can also be used. The electronics required for operating the pump and the control elements are not illustrated here. Use may be made of known means. The pump can be operated with a temporally constant cycle, or, as is known in the prior art, the suction curve may be adapted in the shape, frequency and intensity thereof to the suction behavior of the baby and/or to the requirements of the mother.

In the cover 13, i.e. in the valve plate, there is a first outlet opening 130 which connects the environment to the cover-side part of the pump chamber. The outlet opening 130 serves as a first port for the first line 2. A second outlet opening 131, which likewise connects the cover- and the breast-side part of the pump chamber to the surroundings, respectively, is designed as a second port. The second port is provided with the nonreturn valve 5. Use is made here of a spout valve which is plugged onto a connector. However, other types of valve are also usable.

In use, the breast shield 4 is placed onto the mother's breast such that the breast shield at least surrounds the nipple. Preferably, at maximum the areola is additionally surrounded by the breast shield 4. The vacuum pump 1 is switched on and operated in a known manner. The vacuum generated in the pump chamber evacuates the first line 2 such that there is a negative pressure in the breast shield 4. As a result, milk is expressed from the mother's breast and passes through the breast shield 4 and the coupling part 3 into the first line 2. The milk flows through the first port 130 into the cover-side part of the pump chamber. The expressed milk leaves the pump chamber through the second port 131 and the nonreturn valve 5 and passes into the milk collecting container via the second line 6 (see FIG. 8) or else, depending on the embodiment, directly (see FIG. 9). There is therefore no separate line for transporting the milk. The first line 2 serves at the same time as a suction line and as a milk transport line. After initial pneumatic pumping, the device therefore changes to hydraulic pumping. This is a further approximation to the natural sucking of babies.

The diaphragm 14 in the pump chamber has three functions. First, the diaphragm, forms the diaphragm of the diaphragm vacuum pump and thus generates the vacuum in the pump chamber. Second, the diaphragm serves as a partition wall between the air in the pump-side part of the pump chamber and the milk in the cover-side part of the pump chamber. The diaphragm therefore serves as a means of separating media. and thereby prevents milk from being able to pass into the pump unit. However, the diaphragm also prevents dirt from the pump unit from being able to pass into the first and second lines 2, 6. Third, the cyclic movement of the diaphragm within the pump chamber results in the diaphragm conveying and transporting the milk. Due to the third function of the diaphragm 14, during the expressing operation, the milk collecting container 7, breast shield 4 and vacuum pump 1 can be arranged in positions which are independent of one another. For example, the milk collecting container 7 can be located above the vacuum pump 1 and/or the breast shield 4. The vacuum pump 1 may also be above the milk collecting container 7 and/or the breast shield 4. This enables the mother to express milk even while lying down or, if she is seated, to place the milk collecting container 7 and the vacuum pump 1 onto a shelf or another raised platform out of the reach of small children.

In the examples according to FIGS. 7 to 9, a negative pressure of 0 to 300 mmHg is preferably generated. The pumping frequency is preferably between 5 and 120 cycles per minute.

The nonreturn valve 5 preferably opens only when there is sufficient pressure, i.e. when the pump chamber is sufficiently filled with milk. As a result, the dead volume, which has to be evacuated, can be kept to a minimum.

The breast shield according to the invention is pleasant for the mother to wear and reduces the air- or milk-filled dead volume to a minimum when expressing breast milk.

The invention claimed is:

1. A breast shield for use in a device for expressing human breast milk, wherein the breast shield has a tubular connector and a funnel that is integrally formed thereon for resting on a mother's breast, wherein the funnel widens with a first opening angle toward a free side thereof which faces away from the connector, and wherein there is a passage for the expressed breast milk, the passage extending continuously from a breast-side end of the funnel as far as a pump-side end, being opposite said breast-side end, of the connector and serving to apply a vacuum to the mother's breast, wherein the funnel is more flexible than the connector, wherein the funnel has a length and wherein the funnel has a main region extending over a substantial part of said length with the first opening angle of the passage, and a breast-side end region with a second opening angle of the passage, wherein, when the breast shield is not in use, the first opening angle is smaller than the second opening angle, and wherein, when the breast shield is in use, at least the first opening angle can be enlarged by axial pressure on the breast shield.

2. The breast shield as claimed in claim 1, wherein the funnel has a breast-side diameter of 5 mm to 40 mm and a length of 10 mm to 40 mm.

3. The breast shield as claimed in claim 1, wherein there is a transition region between the connector and funnel, with a third opening angle of the passage, wherein, when not in use, the third opening angle is greater than the first opening angle.

4. The breast shield as claimed in claim 1, wherein the main region directly adjoins the transition region and/or wherein the end region directly adjoins the main region.

5. The breast shield as claimed in claim 1, wherein the connector has a wall thickness which is multiple times greater than a wall thickness of the funnel.

6. The breast shield as claimed in claim 1, further comprising an outer stop which protrudes over the outer circumference of the connector in the transition region between the connector and the funnel.

7. The breast shield as claimed in claim 1, wherein an outer circumference of the connector widens conically toward the funnel.

8. The breast shield as claimed in claim 1, wherein the breast shield is manufactured from silicone.

9. The breast shield as claimed in claim 1, wherein the funnel has a Shore-A hardness of about 50 and the connector has a Shore-A hardness of about 70.

10. A breast shield set with a breast shield as claimed in claim 1 and a coupling part for receiving the connector of the breast shield in a sealing manner, wherein the coupling part is of cylindrical design and is closed on one side by a base such that a blind hole for receiving the connector is formed, and further comprising at least one port opening which is in fluid communication to the passage of the breast shield.

11. The breast shield set as claimed in claim 10, wherein, in the assembled state, a breast-shield-remote front end of the connector ends at a distance from the base of the coupling part.

12. The breast shield set as claimed in claim 10, wherein the blind hole of the coupling part tapers in diameter toward the base.

13. The breast shield set as claimed in claim 10, wherein the coupling part is stiff.

14. The breast shield set as claimed in claim 10, wherein the at least one port opening is arranged eccentrically in the coupling part.

15. The breast shield set as claimed in claim 14, wherein the at least one port opening is arranged in an upper region of the coupling part, and wherein the coupling part has a marking which defines a side of the coupling part to be placed as an upper side.

* * * * *